United States Patent
Spormann et al.

(10) Patent No.: US 7,820,406 B2
(45) Date of Patent: Oct. 26, 2010

(54) EXPRESSION OF HETEROLOGOUS FUNCTIONAL OXYGEN-SENSITIVE PROTEINS IN FILAMENTOUS CYANOBACTERIA

(75) Inventors: Alfred M. Spormann, Stanford, CA (US); Wing-On Ng, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 794 days.

(21) Appl. No.: 11/218,386

(22) Filed: Sep. 2, 2005

(65) Prior Publication Data

US 2007/0054389 A1   Mar. 8, 2007

(51) Int. Cl.
C12P 21/06 (2006.01)
C12P 3/00 (2006.01)
C12N 9/02 (2006.01)
C12N 1/20 (2006.01)

(52) U.S. Cl. .................. 435/69.1; 435/189; 435/252.3; 435/168

(58) Field of Classification Search ........................ None
See application file for complete search history.

(56) References Cited

U.S. PATENT DOCUMENTS 4,778,759 A * 10/1988 Szalay et al. ................ 435/477

OTHER PUBLICATIONS

Golden et al. (Current opinion of Microbiol. 2003, 6, pp. 557-563).*
Ramasubramanian et al. ( J. of Bactrol. 1994, pp. 1214-1223).*
Golden et al. Current opinion of Microbiol. 2003, 6, pp. 557-563.*
Kowal et al. ( JBC 1989 254, 4344-4348).*
Berman-Frank et al., Segregation of nitrogen fixation and oxygenic photosynthesis in the marine cyanobacterium *Trichodesmium*, (2001) Science, 294: 1534-1537.
Berman-Frank et al., Nitrogen fixation and photosynthetic oxygen evolution in cyanobacteria, (2003), Research in Microbiology, 154:157-164.
Cai et al., *Anabaena* sp. Strain PCC 7120 Respondes to Nitrogen Deprivaton with a Cascade-Like Sequence of Transcriptional Activations, (1997), Journal of Bacteriology, 179(1): 267-271.
Golden et al., Independent Regulation of nifHDK Operon Transcription and DNA Rearrangement during Heterocyst Differentiation in th eCyanobacterium *Anabaena* sp. Strain PCC 7120, (1991), Journal of Bacteriology, 173(22): 7098-7105.
Meeks et al., Regulation of Cellular Differentiation in Filamentous Cyanobacteria in Free-Living and Plant-Associated Symbiotic Growth States, (2002) Microbiology and Molecular Biology Review, 66(1): 94-121.
Schneegurt et al. Oscillating Behavior of Carbohydrate Granule Formation and Dinitrogen Fixation in the Cyanobacterium *Cyanothece* sp. Strain ATCC 51142, (1994), Journal of Bacteriology, 176: 1586-1597.
Wolk , Heterocyst Formation, (1996), Annual Reviews, 59-78.
Yoon et al., Heterocyst Pattern Formation Controlled by a Diffusible Peptide, 1998, Science, 282: 935-938.
Yoon et al., Strain PCC 7120 hetY Gene Influences Heterocyst Development, 2003, Journal of Bacteriology, 185(23): 6995-7000.

* cited by examiner

*Primary Examiner*—Rebecca E Prouty
*Assistant Examiner*—Md. Younus Meah
(74) *Attorney, Agent, or Firm*—Bozicevic, Field & Francis LLP; Pamela J. Sherwood (57) ABSTRACT

Functional oxygen-sensitive proteins are expressed in a heterologous diazotrophic cyanobacteria cell in the presence of ambient extracellular oxygen.

12 Claims, 3 Drawing Sheets

SEQUENCE LISTING

<160> NUMBER OF SEQ ID NOS: 1

<210> SEQ ID NO 1
<211> LENGTH: 292
<212> TYPE: DNA
<213> ORGANISM: Anabaena variabilis ATCC 29413

<400> SEQUENCE: 1

```
aggcctagcc tagtagtaga agcagtttag tcattagtca ttagtcatta gtcaatggtc      60
attagtcaac agtgaaaaat caatgctatg gactatggac tatggactca gcactcatca     120
cttaattaca taacgaaccc atcatgaaca ataattctac cggttttct gtagagcgat      180 cgcccctct tcggcgacgt tctacaaacc ctcacagcca tagtcaacag gcgtgagatc      240
caaacacaaa gaccgaccaa ctaaccaacc aattgcagga aaagagcata tg             292
```

EXPRESSION OF HETEROLOGOUS FUNCTIONAL OXYGEN-SENSITIVE PROTEINS IN FILAMENTOUS CYANOBACTERIA

BACKGROUND OF INVENTION

Cyanobacteria are an ancient and diverse class of oxygenic photosynthetic bacteria characterized by their ability to use light energy to split water into oxygen and reductant, which is subsequently consumed in dark reaction of photosynthesis. Some cyanobacteria are also able to reduce atmospheric dinitrogen gas to ammonium ($N_2$ fixation). Nitrogen fixation and oxygenic photosynthesis, however, are intrinsically incompatible, because nitrogenase, the enzyme responsible for reduction of $N_2$, is inactivated by minute concentrations of oxygen. Certain diazotrophic (nitrogen-fixing) cyanobacteria, e.g., the genera *Anabaena* and *Nostoc* in the family Nostocaceae, overcome this incompatibility by differentiating specialized, microxic (low oxygen concentration) cells at intervals within chains of other cells. Nitrogen fixation is confined to these specialized terminally differentiated cells, called heterocysts, and oxygenic photosynthesis takes place in the vegetative cells. Some other filamentous diazotrophic cyanobacteria, such as *Trichodesmium* spp. have evolved similar microxic cells for nitrogen fixation without visible differentiation into heterocysts (Berman-Frank et al. (2001) Science. 294: 1534-1537). An alternative to the spatial separation strategy is the temporal separation of photosynthesis and nitrogen fixation found in unicellular cyanobacteria such as *Cyanothece* sp. ATCC51142, *Gloethece* and *Synechocystis* sp. WH8501 (Berman-Frank et al. (2003). Research in Microbiology. 154:157-164). The diurnal separation of the two incompatible biochemical pathways allows the cyanobacteria to photosynthesize during the day and fix nitrogen at night. Unicellular cyanobacteria achieve nitrogen fixation at night by substaining a high rate of respiration at night, thereby creating a microoxic environment inside the cell for nitrogenase to function (Schneegurt et al. (1994). Journal of Bacteriology. 176: 1586-1597).

The heterocyst achieves a near anoxic state by at least three means. Although heterocysts have a photosystem I that they use to generate ATP, they lack $O_2$-producing photosystem II, which is dismantled during heterocyst differentiation, so that the heterocyst need contend only against $O_2$ produced by neighboring vegetative cells and that dissolved in the environment. Heterocysts also comprise a specialized envelope that limits the influx of gases. Two layers within the envelope have been implicated in $O_2$ protection: an inner layer composed of a hydroxylated glycolipid and an outer layer of polysaccharide. Further, much of the $O_2$ that overcomes these barriers is consumed by the high oxidase activity associated with heterocysts.

The heterocyst forms from vegetative cells. Within one or two generations, vegetative cells deprived of a source of nitrogen differentiate into $N_2$-fixing heterocysts. The program of development begins with sensing nitrogen deprivation and culminates in the expression of the $N_2$ fixation apparatus in the mature heterocyst, utilizing an ordered sequence of events.

Due to the absence of photosystem II, the heterocyst is dependent on adjacent vegetative cells for reduced carbon, just as the vegetative cells are dependent on heterocysts for reduced nitrogen. Nitrogen fixed within the heterocyst as ammonium is first converted to glutamine and then passes as amino acids to adjacent vegetative cells. In return, energy in form of fixed carbon flows from vegetative cells to heterocysts.

The expression of oxygen sensitive proteins in heterologous cells, particularly where the cells can be grown in ambient oxic conditions, is of great interest. The present invention provides such methods and compositions.

SUMMARY OF INVENTION

Compositions and methods are provided for the production of $H_2$ in oxygenic photosynthetic bacteria through activity of a heterologous hydrogenase. Hydrogen can be produced under ambient (extracellular) oxic conditions.

In another embodiment of the invention, methods are provided for the expression of functional, heterologous oxygen-sensitive proteins in a bacterial host, where the ambient environment is oxic.

Photosynthetic bacteria of interest as expression hosts are diazotrophic cyanobacteria that generate substantially anoxic cells, or microoxic cells. Such anoxic cells include heterocyst cells, e.g. *Anabaena, Nostoc*, etc.; the non-hetrocystous diazotrophic cells of filamentous cyanobacteria such as *Trichodesmium* spp.; and the temporally anoxic cells of unicellular cyanobacteria such as *Cyanothece* sp. ATCC51142, *Gloethece; Synechocystis* sp. WH8501; etc. Microoxic cells may be characterized by their ability to synthesize functionally active nitrogenase, i.e. the cells are diazotrophic.

Genetic sequences encoding an oxygen-sensitive protein of interest, e.g. hydrogenase, etc. are introduced into the bacteria by conjugation, transformation, etc. Such coding sequences are operably attached to a promoter that is active in the microoxic cells. Following induction of microoxic cell formation, e.g. by nitrogen deprivation, the oxygen-sensitive protein of interest is expressed in the these cells. Where the expressed heterologous protein is hydrogenase, the enzyme catalyzes production of $H_2$.

In one embodiment, the invention provides a genetically modified filamentous diazotrophic cyanobacterium comprising a heterologous protein coding sequence, e.g. a hydrogenase coding sequence, operably attached to a promoter active in microoxic cells of the cyanobacterium. In another embodiment, the invention provides an episomal vector comprising a coding sequence of a hydrogenase operably attached to a promoter active in microoxic cells of filamentous diazotrophic cyanobacterium.

In another embodiment, hydrogen is produced in photosynthetic bacteria by (i) introducing into said bacteria an episomal vector comprising a coding sequence of a hydrogenase operably attached to a promoter active in microoxic cells of filamentous cyanobacterium; (ii) culturing said bacterium under conditions that induce microoxic cell differentiation; (iii) culturing said bacteria for a period of time sufficient to express the hydrogenase in an active form.

DETAILED DESCRIPTION OF THE EMBODIMENTS

Oxygen-sensitive proteins, including anaerobic enzymes and proteins such as nitrogenases, hydrogenases, etc., are readily oxidized and rendered inactive when exposed to oxic conditions. The methods of the present invention provide for expression of such proteins in the substantially anoxic or microoxic cells of certain cyanobacteria.

Genetic sequences encoding a oxygen-sensitive protein of interest, and operably attached to a promoter active in cyanobacterial microoxic cells, e.g. diazotrophic cells are introduced into a suitable cyanobacteria host cell. The polynucleotide sequence is generally heterologous to the host cell, i.e. the sequence is a genetic sequence from an organism other than a cyanobacteria. The bacteria are then cultured to induce microoxic cell differentiation; and maintained in culture conditions for a period of time sufficient to express the protein of interest. Where the protein is an enzyme of interest, e.g. hydrogenase, the microoxic cells may be maintained for a period of time sufficient to catalyze production of hydrogen. The cyanobacteria may be provided with an exogenous energy source, e.g. fructose, etc., and/or may be provided with a light source sufficient to generate energy photosynthetically.

Cyanobacteria

Organisms useful in the methods of the invention include diazotrophic cyanobacteria. Such cyanobacteria are characterized by the ability to generate microoxic cells, either temporally or spatially, generally in combination with the sensitive of the oxygen-sensitive host cell nitrogenase. The oxygen present in the microoxic cells is substantially below the $O_2$ level in the ambient atmosphere, usually the oxygen level is reduced at least about 10× in the microoxic cells relative to the ambient atmosphere, and may be reduced at least about 100× or more.

Cells of interest include heterocystous filamentous cyanobacteria of the family Nostocaceae, which include species of *Anabaena*, e.g. *Anabaena aequalis; Anabaena affinis; Anabaena aphanizomenoides; Anabaena augstumalis; Anabaena azollae; Anabaena azotica; Anabaena bergii; Anabaena circinalis; Anabaena compacta; Anabaena crassa; Anabaena cylindrica; Anabaena ellipsoides; Anabaena flos-aquae; Anabaena gerdii; Anabaena kisseleviana; Anabaena lemmermannli; Anabaena lutea; Anabaena macrospora; Anabaena mendotae; Anabaena mucosa; Anabaena oscillarioides; Anabaena pertubarta; Anabaena planctonica; Anabaena planktonica; Anabaena scheremetievi; Anabaena siamensis; Anabaena sigmoidea; Anabaena smithii; Anabaena solitaria; Anabaena sphaerica; Anabaena spiroides; Anabaena spirulina; Anabaena torulosa; Anabaena ucrainica; Anabaena variabilis; Anabaena viguieri; Anabaena* strain PCC 7120; etc., species of *Anabaenopsis*, e.g. *Anabaenopsis circularis; Anabaenopsis elenkinii;* etc. species of *Aphanizomenon*, e.g. *Aphanizomenon baltica; Aphanizomenon flos-aquae; Aphanizomenon gracile; Aphanizomenon issatschenkoi; Aphanizomenon ovalisporum*; etc.; species of *Aulosira;* e.g. *Aulosira terrestre*; etc.; species of *Cyanospira*; e.g. *Cyanospira rippkae*; species of *Cylindrospermopsis;* e.g. *Cylindrospermopsis africana; Cylindrospermopsis raciborskii;* species of *Cylindrospermum;* e.g. *Cylindrospermum licheniforme; Cylindrospermum majus; Cylindrospermum stagnale;* species of *Mojavia;* e.g. *Mojavia pulchra;* species of *Nodularia;* e.g. *Nodularia baltica; Nodularia harveyana; Nodularia sphaerocarpa; Nodularia spumigena;* species of *Nostoc*; e.g. *Nostoc calcicola; Nostoc commune; Nostoc cycadae; Nostoc desertorum; Nostoc edaphicum; Nostoc ellipsosporum; Nostoc entophytum; Nostoc flagelliforme; Nostoc indistinguenda; Nostoc lichenoides; Nostoc linckia; Nostoc muscorum; Nostoc paludosum; Nostoc piscinale; Nostoc punctiforme; Nostoc sphaericum;* species of *Raphidiopsis;* e.g. *Raphidiopsis curvata; Raphidiopsis mediterranea;* species of *Richelia;* species of *Trichormus; Trichormus azollae; Trichormus doliolum; Trichormus variabilis;* and the like. The use of *Anabaena* sp. strain PCC 7120 and *Anabaena variabilis* ATCC 29413 are exemplary. *Nostoc punctiforme* strain ATCC 29133; *Nostoc* sp. strain PCC 7121 are also exemplary as transformable host cells.

Organisms useful in the methods of the invention also include diazotrophic non-heterocystous filamentous cyanobacteria such as: *Trichodesmium* spp. (see Berman-Frank et al. (2001) Science. 294: 1534-1537, herein specifically incorporated by reference).

Organisms useful in the methods of the invention also include diazotrophic unicellular cyanobacteria such as: *Cyanothece* sp. ATCC 51142 (Reddy et al. (1993) Journal of Bacteriology. 175:1284-1292.), *Gloeothece membranacea* PCC 7941; *Synechococcus* sp. RF-1.

Heterologous Coding Sequences

Polynucleotides encoding heterologous proteins, i.e. proteins not normally present in the cyanobacterial host cell, are introduced into the cyanobacterial host cells for expression. Proteins of interest are generally redox sensitive, and lack enzymatic activity in the presence of ambient oxygen. One of skill in the art will readily select such enzymes, using publicly available genetic sequences, or isolating such sequences from the desired source by conventional methods. Many of such proteins contain metal complexes that are sensitive to the presence of oxygen. Without limitation, such proteins include: nitrogenases, hydrogenases, vinyl chloride reductase; 1,2-dichloroethene reductive dehalogenase; trichloroethene reductive dehalogenase; tetrachloroethene reductive dehalogenase; benzylsuccinate synthase; ethylbenzene dehydrogenase; oxygen-sensitive ribonucleoside triphosphate reductase; etc.

The substantially anoxic conditions within the heterocyst cells or other mirooxic cells allows oxygen sensitive proteins to be expressed in an active, or functional, form, even where there is oxygen present in the extracellular environment. One may determine the specific activity of a protein in a composition by determining the level of activity in a functional assay, which assay will be determined by the nature of the protein, e.g. production of $H_2$ by a hydrogen, nitrogen fixation by nitrogenase, and the like; quantitating the amount of protein present in a non-functional assay, e.g. immunostaining, ELISA, quantitation on coomasie or silver stained gel, etc., and determining the ratio of biologically active protein to total protein. Generally at least about 1% of the protein will be active, usually at least about 5%, and may be about 25%, about 50%, about 90% or greater.

The heterocyst cells or microoxic cells themselves may serve as a microenvironment for the desired enzymatic activity. For example, in bioremediation the genetically modified cyanobacteria may be introduced to a site requiring enzymatic conversion of a substrate by an oxygen sensitive enzyme. An inoculatum of intact filaments or heterocysts expressing the enzyme of interest will be provided to generate the desired enzymatic conversion.

Alternatively, the protein of interest may be isolated from the microoxic cells, usually under anaerobic conditions.

Vectors

In the present methods, an oxygen-sensitive protein is produced by recombinant methods in a diazotrophic cyanobacteria host cell. The DNA encoding the protein of interest may be obtained from various sources according to the desired protein, e.g. cDNA libraries, genomic libraries, specific or non-specific PCR amplification, oligonucleotide synthesis, etc. As described above, there are many such polypeptides and genetic sequences known in the art. Libraries may be screened with probes designed to identify the gene of interest or the protein encoded by it. Screening a library with the selected probe may be conducted using standard procedures as described in Sambrook et at, Molecular Cloning: A Laboratory Manual (New York: Cold Spring Harbor Laboratory Press, 1989).

Amino acid sequence variants of proteins may be prepared by introducing appropriate nucleotide changes into the coding sequence, or by synthesis of the desired sequence. Such variants represent insertions, substitutions, and/or specified deletions of, residues within or at one or both of the ends of the amino acid sequence of a naturally occurring polypeptide, particularly insertions and/or substitutions within or at one or both ends of a mature sequence. Any combination of insertion, substitution, and/or specified deletion is made to arrive at the final construct, provided that the final construct possesses the desired biological activity as defined herein. The amino acid changes also may alter post-translational processes of the polypeptide. Polypeptides may be produced recombinantly not only directly, but also as a fusion polypeptide with a heterologous polypeptide. In general, the signal sequence may be a component of the vector, or it may be a part of the coding sequence that is inserted into the vector.

The nucleic acid (e.g., cDNA or genomic DNA) encoding the polypeptide is inserted into a replicable vector for expression. Many such vectors are available, e.g. plasmids, cosmids, phages, etc. The vector components generally include, but are not limited to, one or more of the following: an origin of replication and optionally coding sequences for replicative proteins, one or more marker genes, and a promoter operably connected to the coding sequence. Preferably the vector is replicable in a suitable laboratory adapted strain, e.g. *E. coli* or an equivalent host cell, and in the filamentous cyanobacteria host cell.

One example of such a broadly replicative plasmid is RSF1010 (also called R300B and R 1162), which is a small (8,684 bp; Scholz et al. (1989) Gene 75, 271-288) multicopy plasmid that can replicate in most Gram-negative bacteria, including cyanobacteria (Gormley and Davis (1991) *J. Bacteriol.* 173, 6705-6708). The replication of RSF1010 DNA in *Escherichia coli* utilizes three plasmid-encoded proteins, the products of replicative genes repA, repB', and repC (Scherzinger et al. (1991) *Nucleic Acids Res.* 19, 1203-1211). In addition, the minimal origin sequence required to support RSF1010 replication has been identified (Scherzinger et al. (1984) *Proc. Natl. Acad. Sci. U. S. A.* 81, 654-658). This 396-bp sequence (oriV) can be divided into two functional domains. The first domain is made up of three direct repeats of 20 bp and adjacent GC-rich and AT-rich segments of DNA. The iterons are the primary binding site for the plasmid-encoded initiator protein RepC. In addition, RepC promotes localized melting of the AT-rich oriV segment. The second domain contains two oppositely oriented sites for the initiation of DNA synthesis, termed ssiA and ssiB. These sequences, which are on the plasmid I-(upper) and r-(bottom) strand, respectively, can function in a single-stranded form as a template for the synthesis of a unique DNA or mixed RNA/DNA primer by the RepB' protein, and they are the primary positions for the initiation of each plasmid strand. Although both of the ssi signals of RSF1010 are required for normal plasmid replication, they can be replaced by other types of priming signals such as the primosome assembly site from phage $\phi$X174 or the priming signal from phage G4. When both ssi sites are replaced by heterologous priming signals, the function of the chimeric oriV is no longer dependent on RepB' but is still dependent on RepA and RepC. RepB is the full-length product of the repB gene, whereas RepB' results from an in-frame start of translation.

Expression vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g. ampicillin, neomycin, streptomycin, tetracycline, etc. (b) complement auxotrophic deficiencies, or (c) supply critical nutrients not available from complex media.

Construction of suitable vectors containing one or more of the above-listed components employs standard ligation techniques. Isolated plasmids or DNA fragments are cleaved, tailored, and re-ligated in the form desired to generate the plasmids required. For analysis to confirm correct sequences in plasmids constructed, the ligation mixtures are used to transform host cells, and successful transformants selected by ampicillin or tetracycline resistance where appropriate. Plasmids from the transformants are prepared, analyzed by restriction endonuclease digestion, and/or sequenced.

Promoters

Expression vectors will contain a promoter that is recognized by the host organism and is operably linked to the coding sequence of the protein of interest. Promoters are untranslated sequences located upstream (5') to the start codon of a structural gene (generally within about 100 to 1000 bp) that control the transcription of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature.

Promoters of interest are active in cyanobacteria microoxic cells. Such promoters may be selectively active in the microoxic cells, i.e. expression is induced during or following formation of microoxic cells; although constitutively active promoters may also find use.

For a description of strong and regulated promoters active in the cyanobacterium *Anabaena* sp. strain PCC 7120, see Elhai (1993) FEMS Microbiol Lett 114:179-184, herein incorporated by reference. Genes in the cyanobacterium *Anabaena* sp. strain PCC 7120 are designated by a 3-letter suffix followed by a number. Genes that have known functions or have significant sequence similarity to other known genes are given proper gene abbreviations in parenthesis.

The following genes have been shown to be expressed in mature heterocysts of Anabaena sp. strain PCC 7120 (see Ehira et al. (2003) DNA Research Vol. 10: 97-113, herein specifically incorporated by reference). As these genes are expressed in heterocysts, the corresponding promoters of these genes are active in mature heterocysts.

Genes expressed in mature heterocysts include all0349; all0350; all0371; all0372; all0373; all0687(hupL); all0688 (hupS); all0729; all1411; all1436(nifX); all1437(nifN); all1437(nifN); all1438(nifE); all1439; all1440(nifK); all1454(nifD); all1455(nifH); all1456(nifU); all1636; all2511; all2512(patB); all2521; all3127; all5341; all5342; all5343; all5344; all5345; all5346; all5347; all5359(hetI); alr0348(ndhD); alr0370; alr0691; alr0731; alr1404; alr1407 (nifV1); alr1410; alr1442(xisA); alr1635; alr2515(coxAII); alr2516(coxCII); alr2517; alr2518; alr2520; alr2522; alr2524; alr2729; alr2730; alr2731(coxBI); alr2732(coxAI); alr3126; alr5351(hglE); alr5352; alr5353; alr5354(hglD); alr5355(hglC); alr5356; alr5357(hetM); alr5358(hetN); alr5360; asl1412; asl2519; asr0689; asr0690; asr1405; asr1406; asr1408(nifZ); asr1409(nifT); asr2513 (fdxB); asr2523.

Promoters of interest include nitrogenase promoters, as this enzyme is typically expressed only under microoxic conditions. One promoter of interest is the Anabaena nifH promoter (PnifH), which is highly and specifically expressed in heterocysts. The Anabaena sp. strain PCC 7120 structural genes for nitrogenase (nifHDK operon) and for the heterocyst-specific ferredoxin (fdxH) that conveys electrons to nitrogenase are first transcribed between about 18 and 24 h after nitrogen stepdown, which promoters are also of interest. Other promoters demonstrated to be selectively active in heterocyst cells include the *Anabaena* promoters PhetR, PhetC, PpatS, and PxisC. Promoters demonstrated to be active in vegetative cells and heterocysts include the Anabaena promoters PpsaA; PpsaB; PpsaC; PhetL; and Prbc.

Transformation or Conjugation

Methods of transferring genetic material into bacterial cells are well known in the art, including transfection, e.g. by $Ca^{++}$, electroporation, etc.; infection with viral vectors; conjugative mating, etc. Any of these methods may be used as appropriate for the desired host cell.

For example, genes and transposons are routinely transferred to Anabaena by conjugal transfer of plasmids from *Escherichia coli* or another suitable host. Suitable methods for such transfer are described, for example, by Elhai and Wolk P (1988) Methods in Enzymology. 167: 747-754; and Elhai et al. (1997) J. Bacteriol 179:1998-2005, each herein incorporated by reference.

In one example of a conjugation protocol, prior to the day of transfer, an exponentially growing culture of *Anabaena* or other filamentous cyanobacteria is fragmented to an average of two to three cells per filament. Fragmented filaments are pelleted, resuspended in fresh medium, and allowed to recover overnight under growth conditions. The next day the cells are harvested and resuspended in a small volume. Overnight cultures are prepared of the donor bacteria, e.g. *E. coli*, etc. carrying the plasmid to be transferred, a conjugal plasmid, and a helper plasmid if desired. For each mating, the donor bacteria are washed and centrifuged, then the pellet mixed with an aliquot of the cyanobacterial suspension containing short filaments derived from fragmentation were added and mixed. The resulting mating mixtures are transferred to petri dishes containing suitable growth medium. The mixtures were allowed to dry on the plate and then incubated under cyanobacteria growth conditions for about 24 h. The mixtures are washed from the surface of the plates, and the resulting suspensions serially diluted, and plated with selective media. The plates are incubated under growth conditions for up to 3 weeks, and colonies then recovered.

Certain strains of *Anabaena* and related organisms have restriction enzymes that can limit efficiency of conjugation, e.g. AvaI, AvaII, and AvaIII, etc. Expression vectors of the present invention may be modified to minimize the presence of restriction sites for these enzymes. Alternatively, the plasmids may be grown in a host cell with modifying enzymes that methylate the restriction sites in the plasmid, thereby protecting them from restriction.

Microoxic Cell formation

Microoxic cells are derived from vegetative cells of the cyanobacteria. For example, heterocysts differentiate from vegetative cells of certain filamentous cyanobacteria. The heterocysts are substantially anoxic. Diminution of the rate of entry of $O_2$ requires a close-packed hydrophobic barrier, which is provided by a layer of characteristic glycolipids. The glycolipid layer of the heterocyst envelope is in turn encompassed by a layer of polysaccharide that protects it from physical damage. The cells respire rapidly in order to maintain a low internal $pO_2$. Because they require reductant, normally obtained from oxygenic photosynthesis, the reductant comes from vegetative cells. The entry of reductant and export of fixed nitrogen require that heterocysts and vegetative cells be joined by a narrow channel, or pore, through which small amounts of $O_2$ can also enter heterocysts. To minimize the influx of oxygen, this pore must be kept very narrow. Nitrogenase is distributed throughout the center of the heterocyst; interposed between it and the pore is a honeycomb of membranes containing oxidases that reduce $O_2$.

When heterocyst-forming cyanobacteria are grown with fixed nitrogen, the vegetative cells grow organized in filaments. When filaments are deprived of fixed nitrogen, cells at semi-regular intervals along the filaments, or terminal cells, differentiate into heterocysts.

Induction of heterocyst formation is performed by moving a culture of vegetative cells to a medium that lacks fixed nitrogen. Such media are known in the art, e.g. as set forth in the examples, normal medium prepared in the absence of nitrates or ammonium is sufficient to induce heterocyst formation. A nitrate level lower than 100 nM is necessary to induce heterocysts in *Anabaena* sp. strain PCC 7120 (Meeks et al. (1983) Applied and Environmental Microbiology 45:1351-1359).

Hydrogen Production

A path of particular interest for generation of hydrogen gas is biological hydrogen production from sunlight, enabled by genetically engineered photosynthetic microbes that express hydrogenases—enzymes that catalyze the reversible reduction of protons into $H_2$. Naturally occurring photosystems are unable to meet this need because most $H_2$-evolving hydrogenases are extremely sensitive to $O_2$ For example, 2% $O_2$ completely inhibits all hydrogenase activity within 2 min.; and 0.1% $O_2$ inhibits 60% of the hydrogenase activity within 2 min. The magnitude of inhibition dependent on the $pO_2$, exposure time and the sensitivity of the protein. However, $O_2$ production which is an inherent byproduct of cyanobacterial photosynthesis. By expression in microoxic cells, the present invention provides a method for generating functional hydrogenases that can utilize photosynthesis for energy and water as a source of electrons for the $H_2$ generation.

Hydrogenases catalyse the reversible oxidation/reduction of molecular hydrogen ($H_2$) and play a vital role in anaerobic metabolism. Metal containing hydrogenases are subdivided into four classes: Fe hydrogenases, Ni—Fe hydrogenases, $H_2$-forming methylenetetrahydromethanopterin dehydrogenase (Hmd) and Ni—Fe—Se, hydrogenases. Hydrogen oxidation is coupled to the reduction of electron acceptors such as oxygen, nitrate, sulphate, carbon dioxide and fumarate, whereas proton reduction ($H_2$ evolution) is coupled to molecules such as ferredoxin. The methods of the invention may be applied to any of the hydrogenases.

In one embodiment, the term "hydrogenase" as used herein refers to an enzyme that meets one or more of the criteria provided herein. Using these criteria, one of skill in the art can determine the suitability of a candidate enzyme for use in the methods of the invention. Many enzymes will meet multiple criteria, including two, three, four or more of the criteria, and some enzymes will meet all of the criteria. The terms "hydrogenase" can refer to a full length enzyme or fragment thereof with the capability of catalyzing hydrogen oxidation/reduction.

Hydrogenases of the invention include enzymes having at least about 20% sequence identity at the amino acid level, more usually at least about 40% sequence identity, and preferably at least about 70% sequence identity to one of the following hydrogenases: *Chlamydomonas reinhardtii* iron-hydrogenase (Genbank accession AY055756); *Clostridium pasteurianum* hydrogenase (Genbank accession AAA23248.1); *Megasphaera elsdenii* hydrogenase (Genbank accession AF120457); *Desulfovibrio vulgaris* hydrogenase (Genbank accession CAA26266.1). For example, see Forestier et al. (2003) Eur. J. Biochem. 270 (13), 2750-2758; Meyer et al. (1991) Biochemistry 30:9697-9704; Voordouw et al. (1985) Eur. J. Biochem. 148:515-520; Atta et al. (2000) Biochim Biophys Acta. 1476(2):368-71; Fauque et al. (1988) FEMS Microbiol. Rev. 4, 299-344; Cammack et al. (1994) Methods Enzymol. 243, 43-68; and de Lacey et al. (1997) J. Am. Chem. Soc. 119, 7181-7189, each herein incorporated by reference.

Homology-based identification (for example, by a PILEUP sequence analysis) of enzymes can be routinely performed by those of skill in the art upon contemplation of this disclosure to identify those suitable for use in the methods of the present invention. Such enzymes are usually produced in microorganisms, particularly bacteria. Hydrogenases of the invention also include an enzyme belonging to the enzyme classifications EC 1.12.7.2 and EC 1.12.2.1.

The nucleic acid sequences encoding the above hydrogenases may be accessed from public databases as previously cited. Identification of additional hydrogenases is accomplished by conventional screening methods of DNA libraries or biological samples for DNA sequences having a high degree of similarity to known hydrogenase sequences.

The sequence of hydrogenases may be altered in various ways known in the art to generate targeted changes in sequence. The sequence changes may be substitutions, insertions or deletions. Such alterations may be used to alter properties of the protein, by affecting the stability, specificity, etc.

Techniques for in vitro mutagenesis of cloned genes are known. Examples of protocols for scanning mutations may be found in Gustin et al., Biotechniques 14:22 (1993); Barany, Gene 37:111-23 (1985); Colicelli et al., Mol Gen Genet 199: 537-9 (1985); and Prentki et al., Gene 29:303-13 (1984). Methods for site specific mutagenesis can be found in Sambrook et al., Molecular Cloning: A Laboratory Manual, CSH Press 1989, pp. 15.3-15.108; Weiner et al., Gene 126:35-41 (1993); Sayers et al., Biotechniques 13:592-6 (1992); Jones and Winistorfer, Biotechniques 12:528-30 (1992); Barton et al., Nucleic Acids Res 18:7349-55 (1990); Marotti and Tomich, Gene Anal Tech 6:67-70 (1989); and Zhu Anal Biochem 177:120-4 (1989).

The peptides may be joined to a wide variety of other oligopeptides or proteins for a variety of purposes. By providing for expression of the subject peptides, various post-expression modifications may be achieved. For example, by employing the appropriate coding sequences, one may provide farnesylation or prenylation. The peptides may be PEGylated. The peptides may also be combined with other proteins to produce a fusion polypeptide.

Modifications of interest that do not alter primary sequence include chemical derivatization of polypeptides, e.g., acylation, acetylation, carboxylation, etc. Also embraced are sequences that have phosphorylated amino acid residues, e.g. phosphotyrosine, phosphoserine, or phosphothreonine.

Modifications may also be made to the hydrogenase coding sequence. In addition to changes in the polypeptide sequence, silent changes in the polynucleotide coding sequence are also of interest, in order to optimize for codon usage of the bacterial strain from which the extract is derived. For example, where the extract is derived from *E. coli*, the codon usage in the hydrogenase coding sequence may be optimized for *E. coli* translation. Methods for such optimization are known in the art, e.g. as set forth in Grosjean and Fiers (1982) Gene 18(3):199-209; Yadava and Ockenhouse (2003) Infection and Immunity 71(9):4961-4969; Gutierrez et al. Nucleic Acids Research 24(13):2525-2527; and Akashi and Gojobori (2002) PNAS 99(6): 3695-3700.

Also included in the subject invention are peptides that have been modified using ordinary molecular biological techniques and synthetic chemistry so as to improve their resistance to proteolytic degradation or to optimize solubility properties, etc. Analogs of such polypeptides include those containing residues other than naturally occurring L-amino acids, e.g. D-amino acids or non-naturally occurring synthetic amino acids. D-amino acids may be substituted for some or all of the amino acid residues. If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

Iron hydrogenase. The hydrogenases containing no other metal than Fe are called Fe hydrogenases (Fe-Hases), also known as "Fe-only" hydrogenases. Two families of Fe-Hases have been described. Cytoplasmic, soluble, monomeric Fe-Hases are found in strict anaerobes such as *Clostridium pasteurianum* and *Megasphaera elsdenii*. They are extremely sensitive to inactivation by $O_2$ and catalyse both $H_2$ evolution and uptake. Periplasmic, heterodimeric Fe-Hases from *Desulfovibrio* spp., can be purified aerobically but catalyse mainly $H_2$ oxidation.

3-D structures of $H_2$ evolving Fe-Hase I from *Clostridium pasteurianum* (CpI) and *Desulfovibrio desulfuricans* uptake hydrogenase (DdH) are known. The overall structure of CpI resembles a mushroom consisting of four domains: the large active site domain forms "cap" and three smaller domains form "stem". The "stem" domains bind four iron-sulphur clusters and are termed FS4A-FS4B, FS4C and FS2. The N-terminal FS2 domain binds a ($Fe_2S_2$) cluster and shares the overall fold with plant-type ferrodoxins. The FS4A-FS4B domain is adjacent to the active site domain; it contains two ($Fe_4S_4$) clusters and has the overall fold similar to that of bacterial type ferrodoxins. The FS4C domain is placed between the FS2 and FS4A-FS4B domains and consists of two α-helices linked by a loop that binds a single ($Fe_4S_4$) cluster via one His and three Cys residues. The large subunit of DdH lacks FS4C and FS2 clusters and corresponding domains. The small subunit of DdH has an unusual fold consisting of alternating random coil and four α-helices that form a "belt" around the large subunit.

The active site domain of the Fe-Hases contains an unusual Fe—S centre termed the H-cluster. H-cluster consists of the ($Fe_4S_4$) subcluster bridged via the Cys thiolate to the ($Fe_2$) (binuclear iron) subcluster. The two iron atoms are designated Fe1 and Fe2 (proximal and distal with respect to the ($Fe_4S_4$) subcluster) and are ~2.6 Å apart. With the exception of the bridging Cys, the diiron subcluster is coordinated by non-protein ligands. In CpI, both iron atoms are octahedrally coordinated to five CO/CN ligands, three S ligands and one water molecule. Fe1 and Fe2 are bridged by two S atoms and one CO or CN ligand. The two bridging sulphurs themselves are bridged by atom(s) of unknown identity. In DdH, Fe1 and Fe2 are bridged by a small molecule that has been modelled as 1,3-propanedithiol (PDT). Fe1 is octahedrally coordinated while Fe2 has square pyramidal coordination geometry.

Nickel Iron Hydrogenase. The Ni—Fe hydrogenases, when isolated, are found to catalyse both $H_2$ evolution and uptake, with low-potential multihaem cytochromes such as cytochrome $c_3$ acting as either electron donors D or acceptors A, depending on their oxidation state. The Ni—Fe hydrogenases are heterodimeric proteins consisting of small (S) and large (L) subunits. The small subunit contains three iron-sulphur clusters, two $(Fe_4S_4)^{2+/1+}$ and one $(Fe_3S_4)^{1+/0}$; the large subunit contains a nickel-iron centre.

The 3-D structures of the Ni—Fe hydrogenases from *Desulfovibrio gigas* and *Desulfovibrio vulgaris* have been determined. The large subunit is an α/β protein. The active site is dinuclear, containing both Ni and Fe ions placed 2.55-2.9 Å apart. The Ni is pentacoordinated (square pyramidal) with four S atoms of Cys residues being equatorial ligands and the bridging S or O atom an axial ligand. The coordination geometry of the Fe is a slightly distorted octahedron, with three bridging ligands between Ni and Fe (two S of Cys residues and one S or O atom) and three terminal ligands called L1, L2 and L3. In *D. vulgaris* hydrogenase, the larger ligand L1 has been proposed to be S=O, while the smaller ligands L2 and L3 have been assigned as CO or $CN^-$. There is no general agreement on the catalytic mechanism of Ni—Fe hydrogenase. The small subunit consists of two domains, $I_S$ and $II_S$. The α/β twisted open sheet structure of the N-terminal Is domain is similar to that of flavodoxin; the C-terminal $II_S$ domain contains two α-helices and no β-structure. The Fe—S clusters are distributed almost along a straight line, with the ($Fe_3S_4$) cluster located halfway between the two ($Fe_4S_4$) clusters. The $(Fe_4S_4)_{dist}$ cluster is coordinated by one His and three Cys residues. This is the only known example of histidine acting as a ($Fe_4S_4$) cluster ligand in protein structure. A crown of acidic residues surrounds the partially exposed His ligand of the $(Fe_4S_4)_{dist}$ cluster and this might provide a recognition site for the redox partner (cytochrome $c_3$).

It is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

The following examples are offered by way of illustration and not by way of limitation.

EXPERIMENTAL

Example 1

Figure 1:
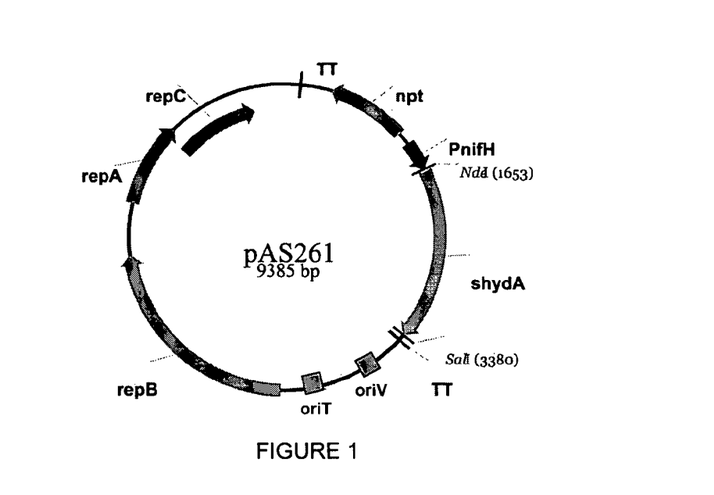
FIG. 1. Map showing the locations of genetic elements on the hydrogenase expression plasmid, pAS261. RSF1010 replicon: oriV (origin of replication); oriT (origin of conjugal transfer); repB, repA and repC (plasmid replication proteins). Transcription module: TT (transcription terminator); npt (neomycin phosphotranferase, antibiotics selection marker); PnifH (nifH promoter from *Anabaena variabilis* ATCC 29413); shydA (synthetic hydrogenase gene based on the hydA gene from *Clostridium pasteurianum*). NdeI and SalI are restriction sites.

Construct for the hydrogenase expression: The following plasmid pAS261 (FIG. 1) was used to express a hydrogenase (shydA) in *Anabaena* sp. strain PCC 7120. The plasmid is consisted of two major modules: 1) RSF1010 replicon (oriV, oriT, repB, repA, repC) which allows the plasmid to replicate in *Anabaena* sp. PCC 7120; and 2) the transcription module (TT, npt, PnifH, shydA, TT) which expresses hydrogenase specifically in mature heterocysts.

Figure 2:
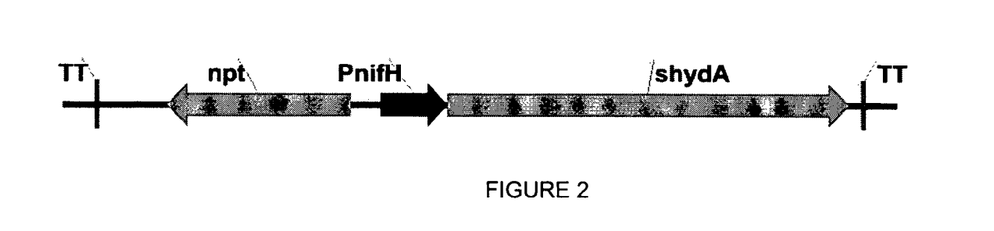
FIG. 2 Detailed map of the transcription module.

The transcriptional fusion between the nitrogenase promoter (PnifH) and the hydrogenase gene (shydA) is shown in FIG. 2. This arrangement places the expression of shydA under the control of PnifH. Therefore, shydA is expressed only in mature heterocysts since PnifH is only functional in mature heterocysts.

Sequence for the nifH promoter: Below is the modified sequence of the PnifH from *Anabaena variabilis* ATCC 29413. Restriction sites were added to the 5' and 3'-ends of the promoter.

(SEQ ID NO: 1)
5'-aggcctagcctagtagtagaagcagtttagtcattagtcattagtca ttagtcaatggtcattagtcaacagtgaaaaatcaatgctatggactatg -continued

```
gactatggactcagcactcatcacttaattacataacgaacccatcatga acaataattctaccggttttctgtagagcgatcgcccctcttcggcga cgttctacaaaccctcacagccatagtcaacaggcgtgagatccaaacac aaagaccgaccaactaaccaaccaattgcaggaaaagagcatatg-3'
```

Conjugation. The hydrogenase expression plasmid pAS261 was transformed into the *Escherichia coli* host NG397 (*E. coli* strain Top10 carrying the conjugal plasmid pRL443, the helper plasmid pRL542 and the methylation plasmid pNG296). The resulting *E. coli* strain NG398 was mated with *Anabaena* sp. strain PCC 7120 using a modified protocol of Elhai and Wolk P (1988) Methods in Enzymology. 167: 747-754.

Cell culture. The minimal medium BG-11 was used to culture *Anabaena* sp. PCC 7120. BG-11 contains fixed nitrogen (nitrate and ammonium) and other minerals cells need. To starve the cell for nitrogen, the cells are harvested and transferred to the fixed nitrogen-free medium, BG-11$_0$. BG-11$_0$ is very similar in chemical composition as BG-11, except it does not have any nitrate or ammonium in it.

| BG-11 | | | |
|---|---|---|---|
| NaNO$_3$ | 1.5 g | Ferric ammonium citrate | 0.006 g |
| K$_2$HPO$_4$ | 0.04 g | EDTA (disodium salt) | 0.001 g |
| MgSO$_4$·7H$_2$O | 0.075 g | NaCO$_3$ | 0.02 g |
| CaCl$_2$·2H$_2$O | 0.036 g | Trace metal mix A5 | 1.0 ml |
| Citric acid | 0.006 g | Agar (if needed) | 10.0 g |
| Distilled water | 1.0 L | TES-KOH Buffer (pH 8.0) | 10 mM |

Adjust pH to 7.1 after sterilization
Trace metal mix A5:

| H$_3$BO3 | 2.86 g | NaMoO$_4$·2H$_2$O | 0.39 g |
|---|---|---|---|
| MnCl$_2$·4H$_2$O | 1.81 g | CuSO$_4$·5H$_2$O | 0.079 g |
| ZnSO$_4$·7H$_2$O | 0.222 g | Co(NO$_3$)$_2$·6H$_2$O | 49.4 mg |

Distilled water to 1 L

Figure 3:
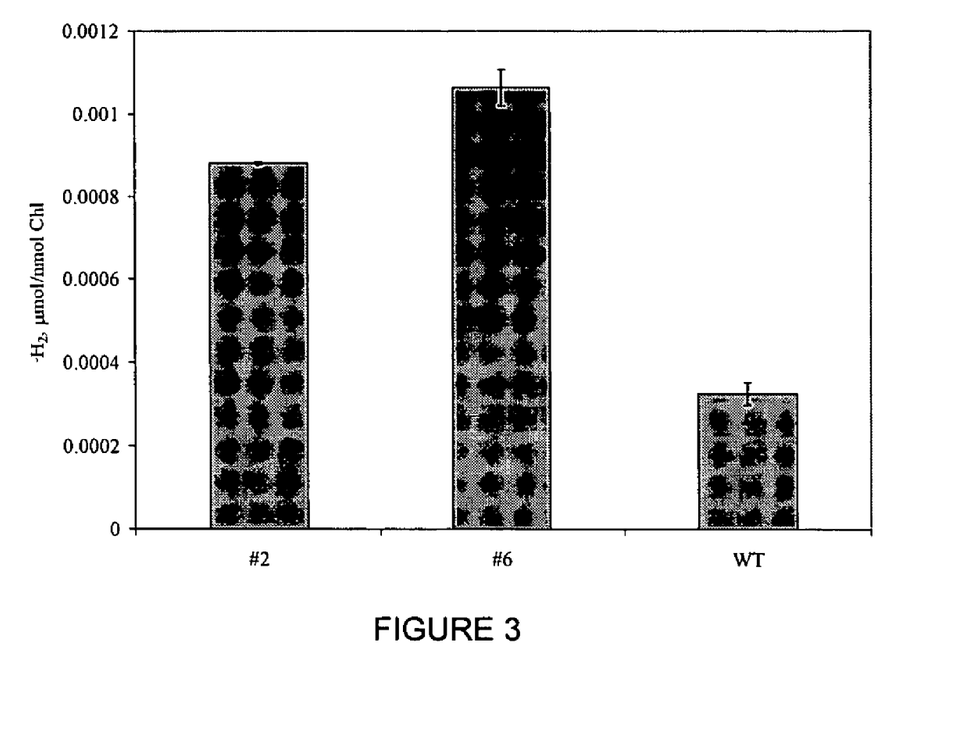
FIG. 3 Normalized hydrogen production from *Anabaena* sp. PCC 7120 isolates carrying the expression plasmid, pAS261 (isolates #2 and #3) and the wildtype (WT).

*Anabaena* sp. strain PCC 7120 isolates carrying the expression plasmid, pAS261, produced 2 to 3-fold more hydrogen (FIG. 3, isolates #2 and #3) than the wildtype. The increase in hydrogen produced results from functional hydrogenase expressed in the heterocysts.

The hydrogenase was expressed by itself, in the absence of accessory proteins exogenous (heterologous) to the cyanobacteria. It appears heterocysts can provide the necessary proteins/factors to synthesize a functional *Clostridium* hydrogenase. Such accessory proteins have been identified as members of the Radical SAM (S-adenosylmethionine) superfamily, and have been identified in a number of hydrogenase producing genomes. Radical SAM proteins are frequently involved in the anaerobic synthesis of complex biomolecules and coordinate unusual (FeS) clusters that are often labile. The accessory proteins HydE, HydF and HydG have been proposed in a number of prokaryotes with iron hydrogenases. In the genomes of *Bacteroides thetaiotaomicron, Desulfovibrio vulgaris, Desulfovibrio desulfuricans*, and *Shewanella oneidensis* the HydE, HydF, and HydG genes form putative operons with (Fe) hydrogenase structural genes, although within the majority of the organisms the accessory proteins are found separated from the structural genes.

Example 2

Expression of functional vinyl chloride reductase (vcrA) in *Anabaena* sp. strain PCC 7120.

Construct for the hydrogenase expression: The following plasmid (FIG. 4) is used to express a vinyl chloride reductase gene (vcrA) in *Anabaena* sp. strain PCC 7120. The plasmid is consisted of two major modules: 1) RSF1010 replicon (oriV, oriT, repB, repA, repC) which allows the plasmid to replicate in *Anabaena* sp. PCC 7120; and 2) the transcription module (TT, npt, PnifH, shydA, TT) which expresses vinyl chloride reductase specifically in mature heterocysts.

Figure 4:
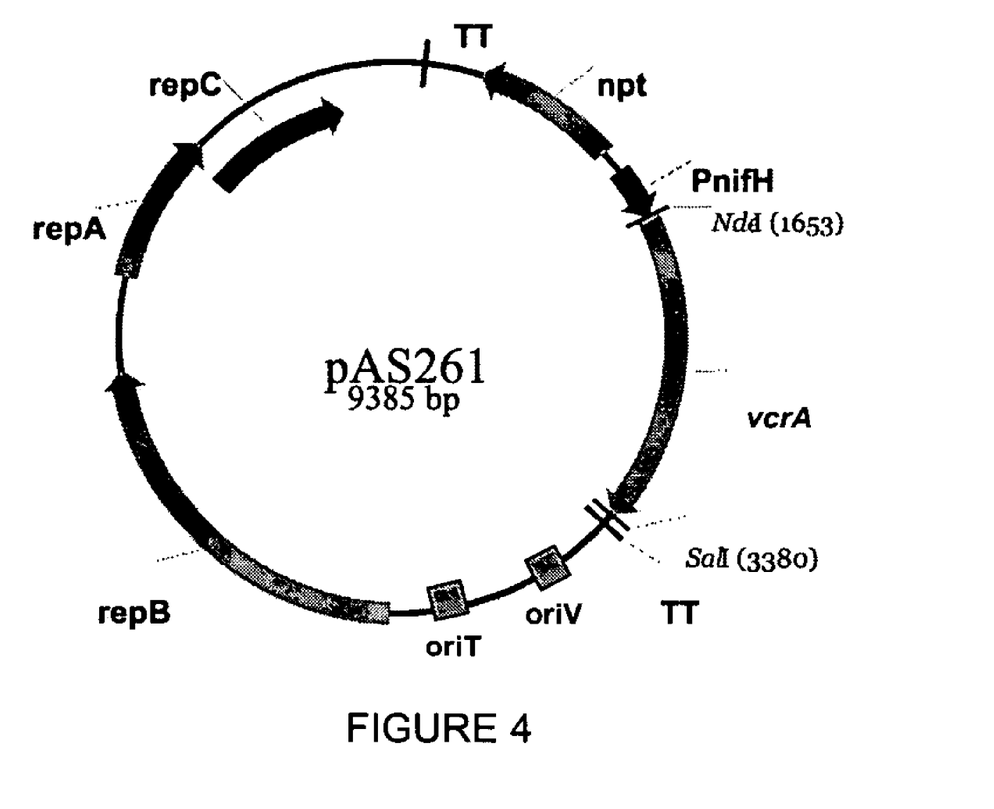
FIG. 4 Map showing the locations of genetic elements on the vinyl chloride reductase expression plasmid. RSF1010 replicon: oriV (origin of replication); oriT (origin of conjugal transfer); repB, repA and repC (plasmid replication proteins). Transcription module: TT (transcription terminator); npt (neomycin phosphotranferase, antibiotics selection marker); PnifH (nifH promoter from *Anabaena variabilis* ATCC 29413); vcrA (vinyl chloride reductase gene from *Dehalococcoides* sp. Strain VS). NdeI and SaII are restriction sites.

The transcriptional fusion between the nitrogenase promoter (PnifH) and vinyl chloride reductase gene (vcrA) places the expression of vcrA under the control of PnifH. Therefore, vcrA is expressed only in mature heterocysts since PnifH is only functional in mature heterocysts.

Conjugation. The vinyl chloride reductase expression plasmid is transformed into the *Escherichia coli* host NG397 (*E. coli* strain Top10 carrying the conjugal plasmid pRL443, the helper plasmid pRL542 and the methylation plasmid pNG296). The resulting *E. coli* strain is mated with *Anabaena* sp. strain PCC 7120 using a modified protocol of Elhai and Wolk P (1988) Methods in Enzymology. 167: 747-754.

*Anabaena* sp. strain PCC 7120 isolates carrying the vinyl chloride reductase expression plasmid are induced in fixed nitrogen-free medium, BG-11$_0$. Enzymatic activity of vinyl chloride reductase is measured using assays described in Müller et al. (2004) Applied and Environmental Microbiology. 70: 4880-4888.

It is evident that subject invention provides a convenient and effective way of expressing oxygen sensitive proteins under ambient oxic conditions. The subject methods will provide a number of benefits, including reduction of unnecessary expense, and the ability to utilize photosynthesis as an energy source for chemicals reactions such as production of H$_2$ from H$_2$O. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of expressing a functional oxygen-sensitive protein under ambient oxic conditions, the method comprising:
   introducing into a diazotrophic filamentous cyanobacteria, of the genus *Nostoc* or *Anabaena*, polynucleotide sequences encoding a heterologous oxygen-sensitive protein operably linked to a promoter selectively active in microoxic cells;
   culturing said diazotrophic cyanobacteria under conditions that induce microoxic cell formation;
   selectively expressing said oxygen-sensitive protein in said microoxic cells,
   wherein said oxygen-sensitive protein is expressed as a functional protein in said microoxic cells.

2. The method according to claim 1, wherein said vector is introduced into said bacteria by conjugation, transformation or transduction.

3. The method according to claim 1, wherein said promoter is a nitrogenase promoter.

4. The method according to claim 1, wherein said conditions that induce microoxic cell formation are cultured in the absence of fixed nitrogen.

5. The method according to claim 1, wherein said culture is provided with a light source sufficient to generate energy photosynthetically.

6. A method of expressing a functional oxygen-sensitive hydrogenase protein under ambient oxic conditions, the method comprising:
   introducing into a diazotrophic cyanobacteria, of the genus *Nostoc* or *Anabaena*, polynucleotide sequences encoding a heterologous oxygen-sensitive hydrogenase protein operably linked to a promoter selectively active in microoxic cells;
   culturing said diazotrophic cyanobacteria under conditions that induce microoxic cell formation;
   selectively expressing said oxygen-sensitive hydrogenase protein in said microoxic cells
   wherein said oxygen-sensitive hydrogenase protein is expressed as a functional protein in said microoxic cells.

7. The method according to claim 6, wherein said hydrogenase is an iron only hydrogenase.

8. The method according to claim 7, wherein said hydrogenase is a *Clostridium* hydrogenase.

9. The method according to claim 1, wherein said diazotrophic cyanobacteria is *Anabaena* sp, strain PCC 7120, *Anabaena variabilis* ATCC 29413, or *Nostoc punctiforme* strain ATCC 29133.

10. The method according to claim 6, wherein said promoter is a nitrogenase promoter.

11. The method according to claim 10, wherein said diazotrophic cyanobacteria is *Anabaena* sp, strain PCC 7120, *Anabaena variabilis* ATCC 29413, or *Nostoc punctiforme* strain ATCC 29133.

12. The method according to claim 1, wherein said conditions that induce microoxic cell formation are cultured in a medium with a nitrate level lower than 100 nM.

* * * * *